(12) United States Patent
Ruyak

(10) Patent No.: US 12,115,186 B1
(45) Date of Patent: Oct. 15, 2024

(54) TOPICAL BURN CREAM

(71) Applicant: CYNDIE HOLST FAMILY TRUST, Lake Barrington, IL (US)

(72) Inventor: John Edwin Ruyak, Lake Barrington, IL (US)

(73) Assignee: CYNDIE HOLST FAMILY TRUST, Lake Barrington, IL (US)

( * ) Notice: Subject to any disclaimer, the term of this patent is extended or adjusted under 35 U.S.C. 154(b) by 153 days.

(21) Appl. No.: 18/094,349

(22) Filed: Jan. 7, 2023

(51) Int. Cl.
| | |
|---|---|
| *A61K 33/30* | (2006.01) |
| *A61K 9/00* | (2006.01) |
| *A61K 31/63* | (2006.01) |
| *A61K 31/635* | (2006.01) |
| *A61K 31/717* | (2006.01) |
| *A61K 31/79* | (2006.01) |
| *A61K 33/18* | (2006.01) |
| *A61K 33/38* | (2006.01) |
| *A61K 35/644* | (2015.01) |
| *A61K 36/28* | (2006.01) |
| *A61K 36/886* | (2006.01) |

(52) U.S. Cl.
CPC ............ *A61K 33/30* (2013.01); *A61K 9/0014* (2013.01); *A61K 31/63* (2013.01); *A61K 31/635* (2013.01); *A61K 31/717* (2013.01); *A61K 31/79* (2013.01); *A61K 33/18* (2013.01); *A61K 33/38* (2013.01); *A61K 35/644* (2013.01); *A61K 36/28* (2013.01); *A61K 36/886* (2013.01)

(58) Field of Classification Search
CPC ...... A61K 33/30; A61K 9/0014; A61K 31/63; A61K 31/635; A61K 31/717; A61K 31/79; A61K 33/18; A61K 33/38; A61K 35/644; A61K 36/28; A61K 36/886
See application file for complete search history.

(56) References Cited

U.S. PATENT DOCUMENTS

| 4,049,802 A | 9/1977 | Fox, Jr. |
| 2007/0110685 A1 | 5/2007 | Auspitz et al. |
| 2016/0022676 A1 | 1/2016 | DeMeo |

FOREIGN PATENT DOCUMENTS

| CN | 1045887 C | 10/1999 |
| CN | 1386506 A | 12/2002 |
| CN | 102349920 B | 11/2013 |

*Primary Examiner* — Jeffrey T. Palenik
*Assistant Examiner* — Kimberly Barber
(74) *Attorney, Agent, or Firm* — UNDERWOOD & ASSOCIATES, LLC

(57) ABSTRACT

A topical burn cream includes zinc oxide in an amount equal to about 72 percent by weight; sulfanilamide in an amount equal to about 18 percent by weight; and iodine in an amount equal to about 0.09 percent by weight.

5 Claims, 1 Drawing Sheet

TOPICAL BURN CREAM

TECHNICAL FIELD

The present invention relates to a topical burn cream for the treatment of burns. More particularly, the invention relates to a burn cream comprising a mixture of zinc oxide, sulfanilamide, and iodine, which have been shown to have antibacterial, anti-inflammatory, and wound-healing properties.

BACKGROUND

Burn creams are topical medications used to treat burns. They are applied directly to the burned area of the skin to help soothe pain, reduce inflammation, and prevent infection. There are several different types of burn creams available, including those that contain aloe vera, antibiotics, or silver sulfadiazine.

Burns can be caused by a variety of factors, including heat, chemicals, electricity, and radiation. The severity of a burn is determined by how deep it penetrates into the skin. First-degree burns affect only the outer layer of skin, while second-degree burns extend into the second layer of skin. Third-degree burns are the most severe and affect all layers of skin and underlying tissue.

First-degree burns can often be treated at home with over-the-counter burn creams and cool, running water. Second-degree burns may require more intensive treatment, such as a prescription burn cream or a visit to a healthcare provider. Third-degree burns should always be treated by a healthcare professional and may require surgery to repair damaged skin and tissue.

Burn creams are an important part of burn treatment because they can help to prevent infection, which can be a serious complication of burns. Burns can break down the skin's natural barrier, making it easier for bacteria to enter the body and cause an infection. Burn creams that contain antibiotics can help to kill bacteria and prevent infection from developing.

In addition to preventing infection, burn creams can also help to reduce pain and inflammation associated with burns. Many burn creams contain ingredients that have pain-relieving and anti-inflammatory properties, such as aloe vera or lidocaine. These ingredients can help to reduce redness, swelling, and discomfort associated with burns.

Burn creams are generally safe and effective when used as directed. However, it is important to seek medical attention if a burn is large, deep, or does not heal within a few days. These burns may require more intensive treatment, such as wound dressings, skin grafts, or surgery. Overuse of burn creams can lead to skin irritation and allergic reactions. It is also important to avoid applying burn creams to broken skin or open wounds, as this can increase the risk of infection.

SUMMARY

In general, the present invention provides a topical burn cream comprising a mixture of zinc oxide, sulfanilamide, and iodine. The burn cream is applied directly to the burned area of the skin to help reduce pain, inflammation, and the risk of infection.

In one embodiment, the burn cream comprises 1 pound of zinc oxide, four ounces of sulfanilamide, and two ounces of iodine. In another embodiment, the burn cream further comprises one or more additional active ingredients, such as aloe vera or lidocaine.

In use, the burn cream is applied to the affected area as needed. The burn cream is generally well tolerated and has been shown to be effective at reducing pain, inflammation, and the risk of infection in burn victims.

The burn cream of the present invention has several advantages over existing burn creams. In particular, the use of a mixture of zinc oxide, sulfanilamide, and iodine allows the burn cream to be more effective at reducing pain, inflammation, and the risk of infection, and promoting healing. Additionally, the burn cream is easy to use and has a good safety profile.

Unless otherwise defined, all technical and scientific terms used herein have the same meaning as commonly understood by one of ordinary skill in the art. Although methods and materials similar or equivalent to those described herein can be used in the practice or testing of any described embodiment, suitable methods and materials are described below. In addition, the materials, methods, and examples are illustrative only and not intended to be limiting. In case of conflict with terms used in the art, the present specification, including definitions, will control.

The foregoing summary is illustrative only and is not intended to be in any way limiting. In addition to the illustrative aspects, embodiments, and features described above, further aspects, embodiments, and features will become apparent by reference to the drawings and the following detailed description and claims.

BRIEF DESCRIPTION OF DRAWINGS

The present embodiments are illustrated by way of the figures of the accompanying drawings, which may not necessarily be to scale, in which like references indicate similar elements, and in which.

DETAILED DESCRIPTION OF ILLUSTRATIVE EMBODIMENTS

Figure 1:
FIG. 1 is a photograph of an untreated pediatric subject showing chapped skin on the face, neck and chest area.

When human skin is burned, it reacts in a number of ways. First, the skin becomes red and painful due to inflammation and damage to the blood vessels. The burn may also cause the skin to blister, which is a result of the accumulation of fluid under the skin. If the burn is deep, the skin may appear white or charred. As the burn begins to heal, the skin may become dry and itchy. In severe cases, the burn may cause scarring and loss of pigment in the affected area. The extent of the damage to the skin and the severity of the burn will depend on the intensity of the burn and the duration of exposure to the heat source. Burns can be classified into three categories: first-degree, second-degree, and third-degree. First-degree burns are the mildest, causing redness and swelling of the skin. Second-degree burns are more severe, causing blisters and deeper layers of the skin to be damaged. Third-degree burns are the most severe, causing damage to all layers of the skin and underlying tissues. Treatment for burns may include wound care, pain management, and skin grafting, depending on the severity of the burn.

In a first general aspect, a topical burn cream includes a mixture of sulfanilamide, zinc oxide and iodine in specific proportions, which has been shown to exhibit improved and unexpected healing properties for burns of all types to human skin.

Sulfanilamide is a sulfa drug that is used in the treatment of various bacterial infections. It was one of the first sulfa drugs to be developed and has been used for over 80 years. It is typically used to treat urinary tract infections, bronchitis, and infections of the skin and respiratory tract. Sulfanilamide is not effective against viral infections or infections caused by fungi. It is usually taken orally, but it can also be applied topically to the skin or given intravenously.

The chemical structure of sulfanilamide is $C_6H_7N_3O_2S$. It is a white, crystalline solid that is soluble in water. Sulfanilamide is a sulfa drug, which means it contains a sulfonamide functional group ($—SO_2NH_2$). It is synthesized from p-aminobenzenesulfonyl chloride and aniline, and it can be formulated into a variety of dosage forms, including tablets, capsules, and injectable solutions. Sulfanilamide is used in the treatment of bacterial infections, but it is not effective against infections caused by viruses or fungi. It is believed to work by inhibiting the synthesis of folic acid, which is necessary for the growth and reproduction of bacteria.

Zinc oxide is a chemical compound that is commonly used in a variety of medicinal and cosmetic products. In medicine, it is used as a skin protectant to treat and prevent diaper rash, minor skin irritations, and burns. It is also used to treat a number of skin conditions, including acne, eczema, and rosacea. Zinc oxide can be found in many forms, including creams, ointments, lotions, and sunscreens. When applied to the skin, it forms a protective barrier that helps to keep moisture in and irritants out.

Iodine is a chemical element that is essential for human health. It is necessary for the production of thyroid hormones, which regulate the body's metabolism and energy levels. Iodine is also important for the proper development and function of the brain and nervous system. In medicine, iodine is used to treat and prevent iodine deficiency, which can cause a number of health problems, including goiter (enlargement of the thyroid gland), hypothyroidism, and cognitive defects. Iodine is available in a number of forms, including tablets, liquid solutions, and topical ointments. It is also added to some salt and bread products to help prevent iodine deficiency in populations where it is a common problem.

In a first embodiment, a burn cream including sulfanilamide, zinc oxide and iodine in specific proportions has been used to treat burns to human skin, resulting in more rapid and complete healing compared to other available burn creams. In this embodiment, the proportions of burn cream ingredients found to exhibit the best results were: sulfanilamide in an amount of four (4) U.S. ounces, zinc oxide in the amount of one (1) U.S. pound (sixteen (16) U.S. ounces), and iodine in the amount of two (2) U.S. ounces, each by weight.

In trials, the preceding mixture of the present embodiment was applied topically by a medical doctor to burns of human skin, including burns caused by radiation (e.g., sunburn) and direct heat impingement (e.g., direct contact with fire, a heat source capable of producing burns such as a stove-top element, boiling water or other direct contact) of varying severity. In each case, the cream was applied as soon as possible after the burn was received.

In this and other embodiments, the burn cream of the present embodiment can be used to treat chapped skin of all severity types. Also known as "chapping," this is a common skin condition that occurs when the skin becomes dry, red, and flaky. It is most commonly caused by exposure to cold, dry weather, but it can also be caused by overexposure to the sun, wind, and other environmental factors. Chapping can also be caused by certain medical conditions, such as eczema and dermatitis, or by certain medications that have drying effects on the skin.

When the skin becomes chapped, it can feel rough and tight, and it may be painful or itchy. The skin may also develop cracks or fissures, which can make it more prone to infection. During treatment it is important to avoid further irritation and to use gentle, non-abrasive products to clean and moisturize the skin. The burn cream of the present embodiment is well-suited for treating chapped skin.

It should be understood that the burn cream of the present embodiment has been found to be highly successful in healing not only burns, but skin irritations and inflammatory disorders of the skin such as acne. Examples of skin irritations include but are not limited to irritations from drooling (as may be the case for persons with disabilities or swallowing disorders), hives, chaffing, scratches, reactions with environmental compounds, such as laundry soaps, allergens and other irritants.

Referring now to FIG. 1, a photograph of a pediatric female human subject is shown. The subject suffers from chapped skin due to sensitivity to cold weather and dry atmospheric conditions. The subject's chapped skin can be seen as red, swollen blotches extending from the maxilla and zygoma area, across the mandible and neck, and finally to the chest area. The subject reports the chapped skin as painful when left untreated.

Figure 2:
FIG. 2 is a photograph of the pediatric patient shown in FIG. 1, two hours after application of a burn cream according to the present invention.

FIG. 2 shows the same subject two hours after application of the burn cream of the present embodiment. As can be appreciated, the redness and swelling has considerably subsided and the subject reports relief from pain and itching. Further application of the burn cream provides continued relief and in some cases is fully resolved.

In this and other embodiments, the burn cream of the present invention can include other ingredients to aid in healing of burns and burn wounds. For example, and without limitation, other ingredients can include: aloe vera, a natural plant extract that is often used to soothe and moisturize burnt skin, believed to have anti-inflammatory and wound-healing properties; honey, a natural antimicrobial agent that can help to prevent infection and promote healing in burnt skin; silver, a natural antimicrobial agent that can help to prevent infection and promote healing in burnt skin; silver sulfadiazine, a topical cream that is used to treat burns by inhibiting the growth of bacteria and promoting healing of the skin; hydroxyethyl cellulose, a lubricating agent that is often used in burn dressings to prevent the dressing from sticking to the burnt skin; povidone-iodine, an antiseptic solution that is used to prevent infection in burns by killing bacteria on the skin; and calendula, a natural plant extract that is believed to have anti-inflammatory and wound-healing properties. Such ingredients may be added to the burn cream of the present embodiment in proportions effective to promote further healing or provide other healing advantages.

As recited herein, the burn cream of the present embodiment can consist of the following ingredients in the following proportions:

Zinc oxide in an amount of about 16 ounces, e.g., 13, 14, 15, 16, 17, 18, or 19 ounces;
Sulfanilamide in an amount of about 4 ounces, e.g., 3.2, 3.4, 3.6, 3.8, 4.0, 4.2, 4.4, 4.6 or 4.8 ounces; and
Iodine in an amount of about 2 ounces, e.g., 1.6, 1.7, 1.8, 1.9, 2.0, 2.1, 2.2, 2.3, or 2.4 ounces.

Stated another way, the burn cream of the present embodiment can consist of the following ingredients in the following proportions:

18.1 percent by weight of sulfanilamide, e.g., 17.8, 17.9, 18.0, 18.1, 18.2 percent by weight;

72.7 percent by weight zinc oxide, e.g., 71.5, 72.0, 72.5, 72.7, 73.0 or 73.5 percent by weight; and 0.09 percent by weight iodine.

In some embodiments, the iodine may be used as a colorant with the added benefit that the compound affords with respect to burn treatment as described herein.

In this embodiment, it is the proportions of ingredients recited herein that has led to unexpected and improved results in the healing of various types of burns as compared to other burn creams.

In this and other embodiments, the burn cream of the present embodiment can be applied liberally or sparingly to a burn area, so long as the entire burn area is preferably covered. The burn cream can be reapplied when it is realized that the previous application has soaked into the skin, or at other times as appropriate.

A number of illustrative embodiments have been described. Nevertheless, it will be understood that various modifications may be made without departing from the spirit and scope of the various embodiments presented herein. Accordingly, other embodiments are within the scope of the following claims.

What is claimed is:

1. A topical burn cream, comprising:
   zinc oxide in an amount equal to about 72 percent by weight;
   sulfanilamide in an amount equal to about 18 percent by weight; and
   iodine in an amount equal to about 0.09 percent by weight.

2. The topical burn cream of claim 1, further comprising a secondary ingredient that promotes healing of burn wounds.

3. The topical burn cream of claim 2, wherein said secondary ingredient is selected from the group consisting of: aloe vera, honey, silver, silver sulfadiazine, hydroxyethyl cellulose, povidone-iodine and calendula.

4. The topical burn cream of claim 1, wherein said zinc oxide is present in an amount equal to 72.7 percent by weight; said sulfanilamide is present in an amount equal to 18.1 percent by weight, and said iodine is present in an amount equal to 0.09 percent by weight.

5. A method for treating burns to the skin, comprising:
   applying the topical burn cream according to claim 1 to a burn area.

* * * * *